(12) United States Patent
Iwahashi

(10) Patent No.: US 11,717,260 B2
(45) Date of Patent: Aug. 8, 2023

(54) MALFUNCTION INSPECTION METHOD FOR ULTRASONIC IMAGING SYSTEM, AND ULTRASONIC IMAGING SYSTEM

(71) Applicant: Lily MedTech Inc., Tokyo (JP)

(72) Inventor: Toshihide Iwahashi, Tokyo (JP)

(73) Assignee: LILY MEDTECH INC., Tokyo (JP)

( * ) Notice: Subject to any disclaimer, the term of this patent is extended or adjusted under 35 U.S.C. 154(b) by 0 days.

(21) Appl. No.: 18/071,655

(22) Filed: Nov. 30, 2022

(65) Prior Publication Data

US 2023/0088350 A1 Mar. 23, 2023

Related U.S. Application Data

(63) Continuation of application No. PCT/JP2021/035819, filed on Sep. 29, 2021.

(30) Foreign Application Priority Data

Sep. 30, 2020 (JP) .................................. 2020-165677

(51) Int. Cl.
*A61B 8/00* (2006.01)
*A61B 8/13* (2006.01)
*G01S 15/89* (2006.01)

(52) U.S. Cl.
CPC ............ *A61B 8/13* (2013.01); *G01S 15/8925* (2013.01)

(58) Field of Classification Search
CPC .............................. A61B 8/13; G01S 15/8925
See application file for complete search history.

(56) References Cited

FOREIGN PATENT DOCUMENTS

| JP | H04-367656 A | 12/1992 |
|----|----|----|
| JP | 2002-159492 A | 6/2002 |
| JP | 2011-050542 A | 3/2011 |
| JP | 2019-088169 A | 6/2019 |
| WO | 2019/088169 A1 | 5/2019 |

OTHER PUBLICATIONS

International Search Report and Written Opinion dated Dec. 14, 2021, received for PCT Application PCT/JP2021/035819, filed on Sep. 29, 2021, 8 pages including English Translation.
Notice of Reasons for Refusal dated Jul. 19, 2022, received for JP Application 2021-576517, 4 pages including English Translation.
Decision to Grant dated Aug. 2, 2022, received for JP Application 2021-576517, 5 pages including English Translation.

*Primary Examiner* — Christopher Koharski
*Assistant Examiner* — Taylor Deutsch
(74) *Attorney, Agent, or Firm* — Xsensus LLP

(57) ABSTRACT

An ultrasonic imaging system including an array transducer that includes a plurality of elements each performing at least one of emission or reception of ultrasonic waves, at least some of the plurality of elements being disposed so as to face each other. The ultrasonic imaging system performs malfunction inspection including specifying one emitting element among emitting elements that emit ultrasonic waves and a group of receiving elements that are at least some of the plurality of elements and that receive transmitted waves emitted from the emitting element and transmitted through an imaging region; collecting measurement data of the transmitted waves via the group of receiving elements while switching the emitting element; calculating transfer characteristic values from the measurement data; and detecting a malfunctioning element among the plurality of elements on the basis of the transfer characteristic values.

12 Claims, 7 Drawing Sheets

☐ NORMAL   ▨ MALFUNCTION

MALFUNCTION INSPECTION METHOD FOR ULTRASONIC IMAGING SYSTEM, AND ULTRASONIC IMAGING SYSTEM

CROSS-REFERENCE TO RELATED APPLICATIONS

The present application is a Continuation application of PCT Application No. PCT/JP2021/035819 filed Sep. 29, 2021, which claims priority to Japanese Patent Application No. 2020-165677, filed Sep. 30, 2020, the entire contents of each application are hereby incorporated by reference.

BACKGROUND

1. Field

The present disclosure relates to a malfunction inspection method for an ultrasonic imaging system and to an ultrasonic imaging system.

2. Description of the Related Art

A noninvasive imaging system using ultrasonic waves is widely used in the medical field as an imaging technique for obtaining information about the inside of a subject because it does not require a surgical operation that involves incisions directly made on a living body for observation.

Ultrasonic CT (Computed Tomography) is one method of ultrasonic imaging in which ultrasonic waves are applied to a subject and reflected ultrasonic waves and transmitted ultrasonic waves are used to create a tomographic image of the subject, and is found by recent research to be useful in detecting breast cancer. In ultrasonic CT, a ring-shaped array transducer including elements that emit and receive ultrasonic waves and that are disposed in a ring form is used to create a tomographic image. A large number of elements are disposed to thereby obtain a tomographic image having a high spatial resolution (see, for example, Japanese Unexamined Patent Application Publication No. 10-277042 and International Publication No. 2017/061560).

The elements are mechanical components and may malfunction. An element malfunction may be a cause of a decrease in the image quality of a tomographic image, and therefore, it is desirable to automatically detect an element malfunction by the apparatus and to give the user a notification.

SUMMARY

The present disclosure includes a malfunction inspection method for an ultrasonic imaging system and an ultrasonic imaging system that automatically detect a malfunction in an element that emits and receives ultrasonic waves.

A malfunction inspection method for an ultrasonic imaging system according to the present disclosure is a malfunction inspection method for an ultrasonic imaging system including an array transducer that includes a plurality of elements each performing at least one of emission or reception of ultrasonic waves, at least some of the plurality of elements being disposed so as to face each other, the malfunction inspection method including the steps of: specifying one emitting element among emitting elements that emit ultrasonic waves and a group of receiving elements that are at least some of the plurality of elements and that receive transmitted waves emitted from the emitting element and transmitted through an imaging region; collecting measurement data of the transmitted waves via the group of receiving elements while switching the emitting element; calculating transfer characteristic values from the measurement data; and detecting a malfunctioning element among the plurality of elements on the basis of the transfer characteristic values.

In one aspect of the present disclosure, at least one of an emission characteristic of each of the emitting elements or a reception characteristic of each of the receiving elements is calculated, and the malfunctioning element is detected on the basis of at least one of the emission characteristic or the reception characteristic.

In one aspect of the present disclosure, the emission characteristic is calculated for each of the emitting elements on the basis of a plurality of pieces of the measurement data collected via the group of receiving elements, and the reception characteristic is calculated for each of the receiving elements on the basis of a plurality of pieces of the measurement data collected in response to emission by the plurality of emitting elements.

In one aspect of the present disclosure, the transfer characteristic values each include at least one of a strength, a power, a frequency characteristic, a propagation time, or a phase of a received signal in the measurement data.

In one aspect of the present disclosure, a malfunction state is determined on the basis of at least one of the number or positions of malfunctioning elements.

In one aspect of the present disclosure, a malfunction state is determined on the basis of the number of malfunctioning elements that are continuous.

In one aspect of the present disclosure, a ratio of malfunctioning local elements is calculated by using the number of normal elements sandwiched between malfunctioning elements and the number of the malfunctioning elements between which the normal elements are sandwiched, and a malfunction state is determined on the basis of the ratio of malfunctioning local elements.

In one aspect of the present disclosure, the array transducer includes at least three or more circular-arc ultrasonic array probes each including a plurality of elements, propagation times of the transmitted waves are calculated from the measurement data, and misalignment of the circular-arc ultrasonic array probes is detected from the propagation times.

In one aspect of the present disclosure, ultrasonic waves are emitted while an emitting element in a first circular-arc ultrasonic array probe is switched, and measurement data of transmitted waves is collected via a plurality of elements of a second circular-arc ultrasonic array probe different from the first circular-arc ultrasonic array probe, and a combination of the first circular-arc ultrasonic array probe that emits ultrasonic waves and the second circular-arc ultrasonic array probe that receives transmitted waves is switched.

In one aspect of the present disclosure, the ultrasonic imaging system includes an emitter-receiver circuit that controls, via a switch circuit, emission and reception of ultrasonic waves by the plurality of elements, and a malfunction state of the emitter-receiver circuit is determined on the basis of the emission characteristic and the reception characteristic.

In one aspect of the present disclosure, ultrasonic waves are emitted to a subject disposed in the imaging region while the emitting element is switched by the switch circuit, and subject measurement data including scattered waves is collected by using the group of receiving elements, and a malfunction state of the emitter-receiver circuit or the switch circuit is determined on the basis of the measurement data and the subject measurement data.

In one aspect of the present disclosure, at least one of damage to an element and to a circuit, decreased sensitivity, or increased noise is determined. In accordance with details of a malfunction in the array transducer, display is performed in at least three stages including a normal stage in which imaging is possible, a warning stage in which imaging is possible but a decrease in image quality appears, and an error stage in which imaging is not possible.

An ultrasonic imaging system according to the present disclosure includes: an array transducer that includes a plurality of elements each performing at least one of emission or reception of ultrasonic waves, at least some of the plurality of elements being disposed so as to face each other; an element specifying unit that specifies one emitting element among emitting elements that emit ultrasonic waves and a group of receiving elements that are at least some of the plurality of elements and that receive transmitted waves emitted from the emitting element and transmitted through an imaging region; a data collection unit that collects measurement data of the transmitted waves via the group of receiving elements while switching the emitting element; a transfer characteristic value calculation unit that calculates transfer characteristic values from the measurement data; and a malfunctioning element detection unit that detects a malfunctioning element among the plurality of elements on the basis of the transfer characteristic values.

According to the present disclosure, a malfunction in an element that emits and receives ultrasonic waves can be automatically detected.

DETAILED DESCRIPTION

Figure 1:
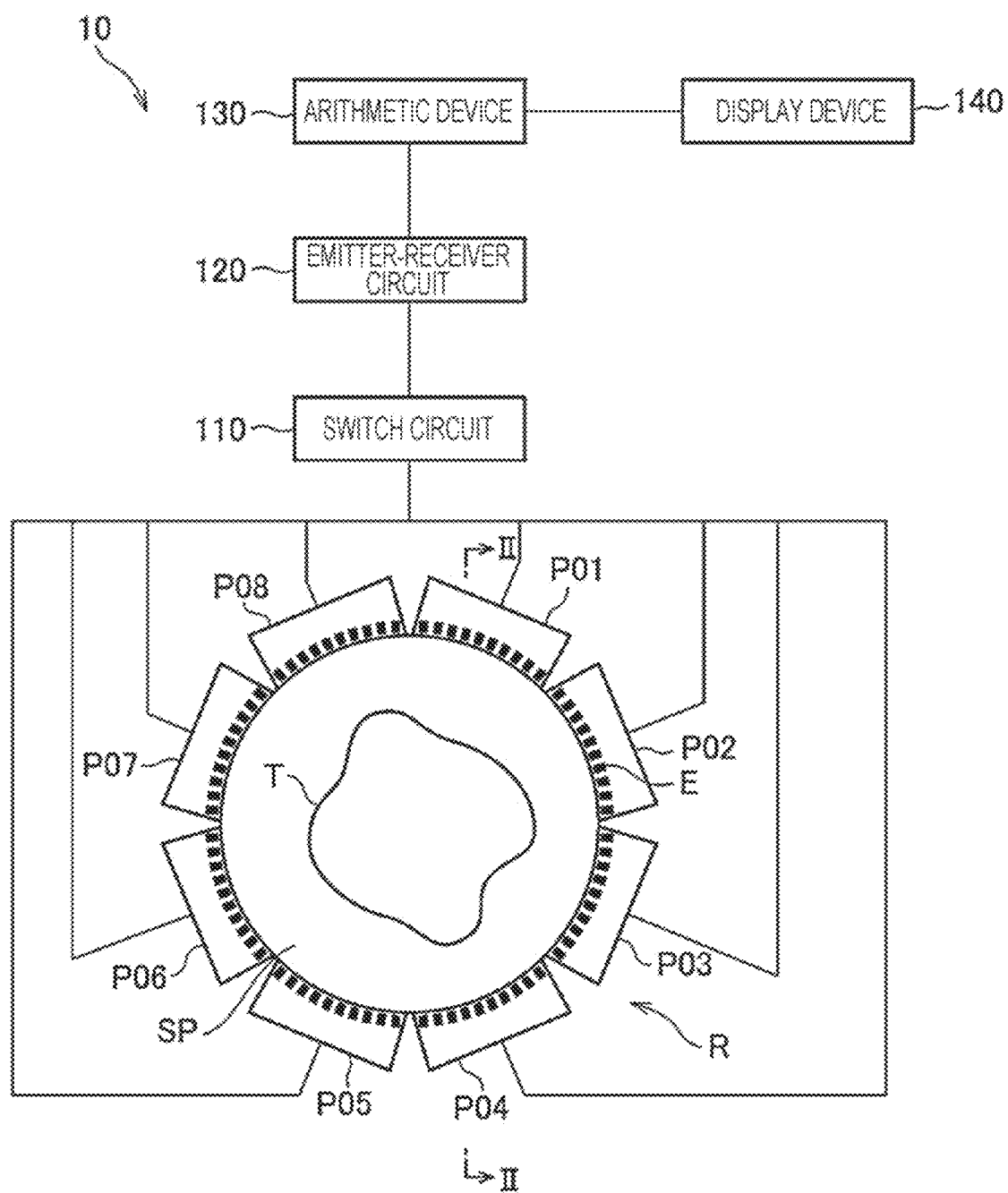
FIG. 1 is a schematic configuration diagram of an ultrasonic imaging system in an embodiment of the present disclosure.

Hereinafter, the present disclosure will be described in further detail with reference to the drawings. In an ultrasonic imaging system according to the present disclosure, ultrasonic pulses are emitted to a subject from one or more ultrasonic transducers that constitute a ring-shaped transducer, and reflected pulses and transmitted pulses from the subject are received by one or more ultrasonic transducers that constitute the ring-shaped transducer. This emission and reception process is repeatedly performed by all ultrasonic transducers of the ring-shaped transducer sequentially to thereby obtain measurement data of the subject, in all directions, disposed in a plane of the ring-shaped transducer and generate a tomographic image. The ring-shaped transducer of the ultrasonic imaging system is constituted by hundreds to thousands of ultrasonic transducers in order to generate a high-resolution tomographic image. A doctor checks the created tomographic image to make a diagnosis.

In the ultrasonic imaging system, emitter circuits for driving the ultrasonic transducers with electric signals and receiver circuits for amplifying electric signals from the ultrasonic transducers are connected to the ring-shaped array transducer with a switch circuit therebetween. The ring-shaped array transducer is aligned with high precision and disposed in a water tank.

Damage and performance degradation occur in ultrasonic transducers with a certain probability due to deterioration over time, an external impact, and so on. An array transducer (typically, an ultrasonic probe) included in a typical ultrasonic diagnosis apparatus is connected to a connector provided in the main unit of the apparatus and used. Therefore, in a case where an ultrasonic transducer of the array transducer malfunctions and is unable to attain target performance, the user can replace the array transducer with a replacement ultrasonic probe.

The ring-shaped array transducer of the imaging system using ultrasonic CT is disposed in the main unit of the apparatus and is constituted by a very large number of elements that are protected so as to be kept watertight. The ring-shaped array transducer is constituted by a large number of transducers, and therefore, has the advantage that an impact of malfunctions in some of the elements on diagnosis performance is small; however, the user may have difficulty in being aware of a decrease in the sensitivity of transducers, a transducer malfunction may be discovered late, and this may affect diagnosis performance. In a case where a malfunction that requires replacement of a transducer occurs, the replacement costs a lot. Further, replacement is technically difficult for the user, and therefore, is to be performed by a serviceperson as maintenance and repair work.

Accordingly, it is desirable for the imaging system using ultrasonic CT to regularly monitor a malfunction state caused by the array transducer and to allow a serviceperson responsible for maintenance or the user to easily check a decrease in the sensitivity of transducers and a malfunction state. In view of such a demand, the present disclosure proposes a technique in which transmitted waves emitted and received by a group of elements including emitting-receiving elements that face each other in the ring-shaped array transducer are used to regularly and automatically inspect the states of the array transducer and circuits connected to the array transducer and determine an impact of a malfunction in the array transducer or in the connected circuits. When changes in a malfunction status over time are grasped, the time for repair and replacement can be predicted, and a period during which the apparatus is unable to be used due to replacement can be reduced. A method for a self-diagnosis (self-determination) of a malfunction or misalignment in the ultrasonic transducers that emit and receive ultrasonic waves will be described below.

As illustrated in FIG. 1, an ultrasonic imaging system 10 according to the present embodiment includes a ring array R, a switch circuit 110, an emitter-receiver circuit 120, an arithmetic device 130, and a display device 140.

The ring array R is an ultrasonic probe in which a large number of ultrasonic transducers are arranged in a ring form, and has a ring shape that measures 80 to 500 mm in diameter in one or more aspects of the disclosed subject matter. Alternatively, or additionally, the ring shape measures 100 to 300 mm in diameter in one or more aspects of the disclosed subject matter. The ultrasonic transducers emit ultrasonic waves into the ring plane and receive ultrasonic waves from the ring plane. The ring array R can have a variable diameter. The ring array R can be in a ring form obtained by combining circular-arc array probes that are sections of a ring. Three or more circular-arc array probes are included, and in the present embodiment, for example, a ring-shaped ultrasonic probe that is a combination of eight circular-arc array probes P01 to P08 is used.

The ring array R that is a combination of circular-arc array probes may have a gap between the circular-arc array probes, and when this is the case, the gap portion is a portion in which no ultrasonic transducer is present in the ring array R. However, even when there is a portion in which no ultrasonic transducer is present, this does not have a large impact on image quality because an image is built by adding up signals of a large number of ultrasonic transducers.

For example, in a case where each of the circular-arc array probes P01 to P08 has 64 rectangular-strip-shaped ultrasonic transducers E (hereinafter also simply referred to as "elements E"), the ring array R is constituted by 512 elements E. The number of elements E provided in each of the circular-arc array probes P01 to P08 is not limited and is 1 to 1000, for example. Taking into consideration measurement in water, each of the circular-arc array probes P01 to P08 accommodates the elements E so as to be watertight.

Each of the elements E has a function of conversion between an electric signal and an ultrasonic signal. The elements E emit ultrasonic waves to a subject T, receive scattered waves that are scattered on the surface or in inner tissue of the subject T (for example, a limb or a breast) and transmitted waves, and convert the waves to electric signals to form measurement data.

Although a description will be given in the present embodiment under the assumption that each element E has a function of both emitting and receiving ultrasonic waves, the present embodiment is not limited to this. For example, emitting elements only having a function of emitting ultrasonic waves and receiving elements only having a function of receiving ultrasonic waves may be used, and a plurality of emitting elements and a plurality of receiving elements may be disposed in a ring form. A configuration in which elements having a function of both emission and reception, emitting elements, and receiving elements coexist may be employed.

Figure 2:
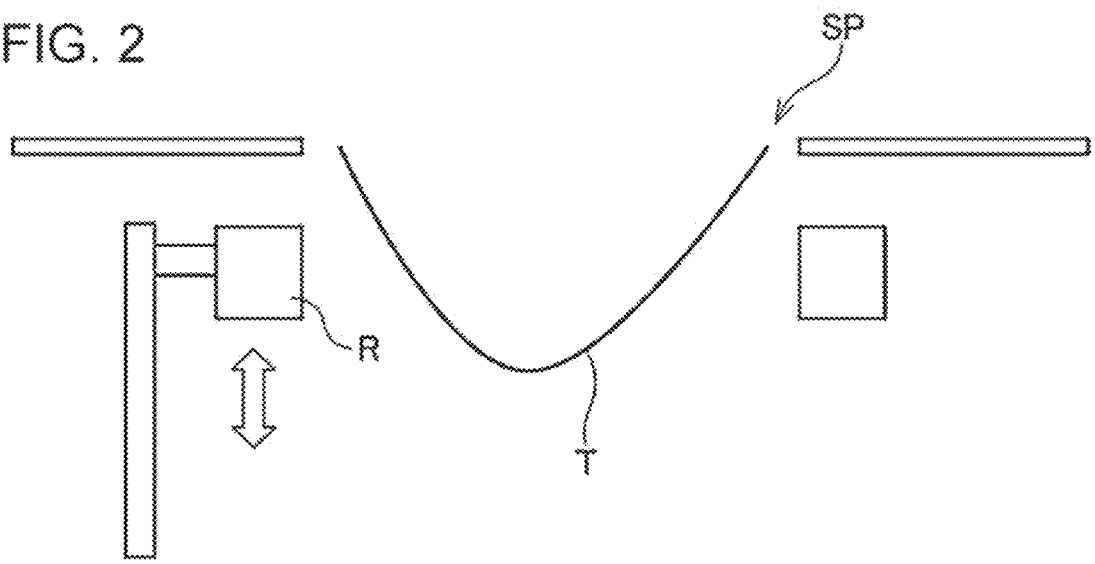
FIG. 2 is a cross-sectional view cut along line II-II in FIG. 1.

FIG. 2 is a cross-sectional view cut along line II-II in FIG. 1. For example, the ring array R may be placed under a bed having a hole such that the hole of the bed and an insertion part SP overlap. An examinee puts a part of their body (subject T) that is an imaging target into the insertion part SP through the hole of the bed.

The insertion part SP into which the subject T is put is provided in the center of the ring array R. The plurality of elements E of the ring array R are provided around the insertion part SP along the ring at regular intervals. On the inner periphery of the ring array R, convex lenses called acoustic lenses are fixed to the surface. When the surface of the inner periphery of the ring array R is thus treated, ultrasonic waves emitted by each element E can be converged within the plane that includes the ring array R.

The ring array R is connected to the emitter-receiver circuit 120 with the switch circuit 110 therebetween. The emitter-receiver circuit 120 (control unit) sends control signals (electric signals) to the elements E of the ring array R to control emission and reception of ultrasonic waves. For example, the emitter-receiver circuit 120 specifies the frequency and magnitude of emitted ultrasonic waves, the type of wave (for example, continuous wave or pulsed wave), and so on for the elements E.

The switch circuit 110 is connected to each of the plurality of elements E of the ring array R, transfers a signal from the emitter-receiver circuit 120 to certain elements E and drives the elements E to thereby make the elements E emit and receive signals. For example, the switch circuit 110 switches elements E to which a control signal from the emitter-receiver circuit 120 is fed, thereby making some of the plurality of elements E function as emitting elements that emit ultrasonic waves and making a plurality of (for example, all) elements E perform reception.

The ring array R is placed so as to be moved upward and downward by, for example, a stepping motor. When the ring array R is moved upward and downward, data of the entire subject T can be collected.

Figure 3:
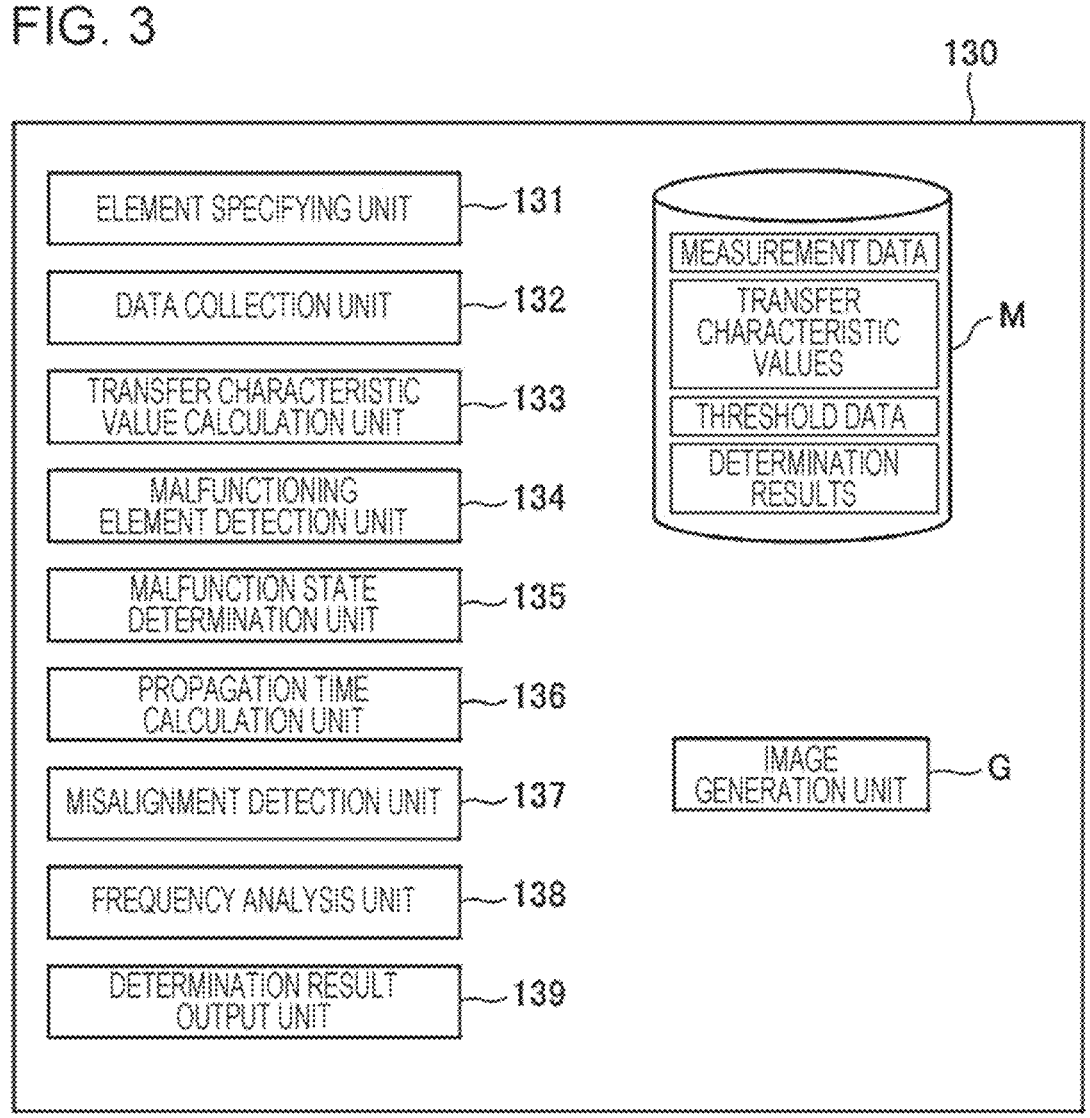
FIG. 3 is a functional block diagram of an arithmetic device.

The arithmetic device 130 is a computer that includes a CPU, a memory M, a communication unit, and so on. The memory M includes a RAM, a ROM, a hard disk, and so on, and the CPU executes a program stored in the memory M to thereby implement the functions of, for example, an element specifying unit 131, a data collection unit 132, a transfer characteristic value calculation unit 133, a malfunctioning element detection unit 134, a malfunction state determination unit 135, a propagation time calculation unit 136, a misalignment detection unit 137, a frequency analysis unit 138, a determination result output unit 139, and an image generation unit G illustrated in FIG. 3. It should be appreciated that the functionality of the elements disclosed herein (e.g., the arithmetic device 130) may be implemented using circuitry or processing circuitry which includes general purpose processors, special purpose processors, integrated circuits, ASICs ("Application Specific Integrated Circuits"), conventional circuitry and/or combinations thereof which are configured or programmed to perform the disclosed functionality. Processors are considered processing circuitry or circuitry as they include transistors and other circuitry therein. The processor may be a programmed processor which executes a program stored in a memory. In the disclosure, the circuitry, circuits, units, or means are hardware that carry out or are programmed to perform the recited functionality. The hardware may be any hardware disclosed herein or otherwise known which is programmed or configured to carry out the recited functionality. When the hardware is a processor which may be considered a type of circuitry, the circuitry, circuits, means, or units are a combination of hardware and software, the software being used to configure the hardware and/or processor.

The element specifying unit 131 specifies elements (emitting elements) that emit ultrasonic waves and elements (receiving elements) that receive ultrasonic waves. That is, the element specifying unit 131 switches elements to be used in emission or reception of ultrasonic waves. The data collection unit 132 collects via the switch circuit 110 and the emitter-receiver circuit 120, measurement data obtained by the plurality of receiving elements and stores the measurement data in the memory M.

The image generation unit G rebuilds an ultrasonic CT image from measurement data by using a publicly known method. For example, the image generation unit G makes corrections including emission acoustic velocity correction and a delay treatment to measurement data, rebuilds the measurement data obtained on each occasion of emission, and generates an image. A large number of elements E that emit and receive ultrasonic waves are disposed, and the presence of a malfunctioning element E may decrease the image quality of the generated image. The ultrasonic imaging system according to the present embodiment determines by itself a malfunction in an element E and the presence of misalignment.

As typical examples of malfunctions in the ring-shaped ultrasonic probe and in the connected circuits, (1) to (4) below are assumed.
(1) Ultrasonic wave emission and reception failures due to damage to an ultrasonic transducer of the ring-shaped ultrasonic probe.
(2) Lowered emitted and received signals and increased noise due to performance degradation of an ultrasonic transducer of the ring-shaped ultrasonic probe (for example, increased attenuation in the multilayer structure of an ultrasonic transducer or a crack in an element).
(3) Damage to an emitter circuit or a receiver circuit in the emitter-receiver circuit and increased noise.
(4) Damage to the switch circuit.

In the present embodiment, ultrasonic transducers of the ring-shaped ultrasonic probe are disposed so as to face each other, and therefore, ultrasonic pulses are emitted from one ultrasonic transducer in water, the ultrasonic pulses are received by the opposite ultrasonic transducer, and from the transfer characteristic of the ultrasonic pulses, damage to and performance degradation of the individual transducer is diagnosed (determined).

Figure 4:
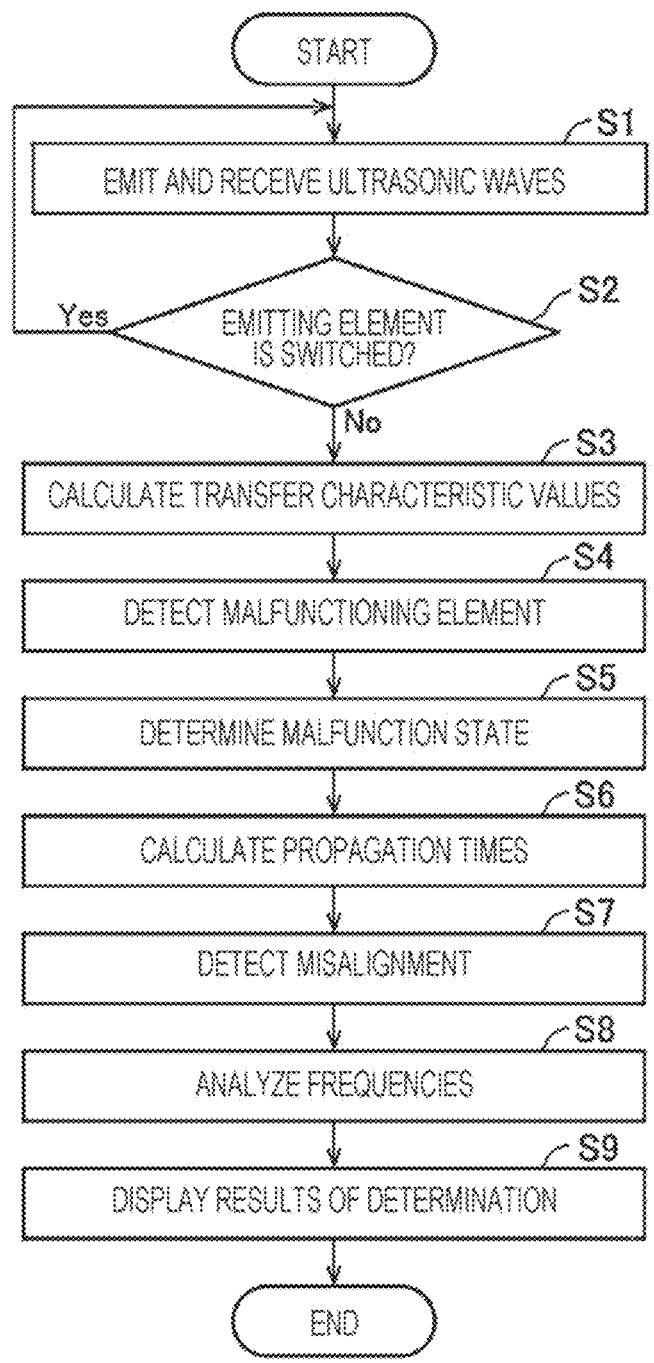
FIG. 4 is a flowchart for explaining a self-diagnosis method by the ultrasonic imaging system.

A specific method for a diagnosis made on ultrasonic transducers of the ring-shaped ultrasonic probe according to the present embodiment will be described with reference to the flowchart illustrated in FIG. 4. This diagnosis process is regularly performed and is performed, for example, once a day, upon starting the system, or each time imaging is completed.

Figure 5:
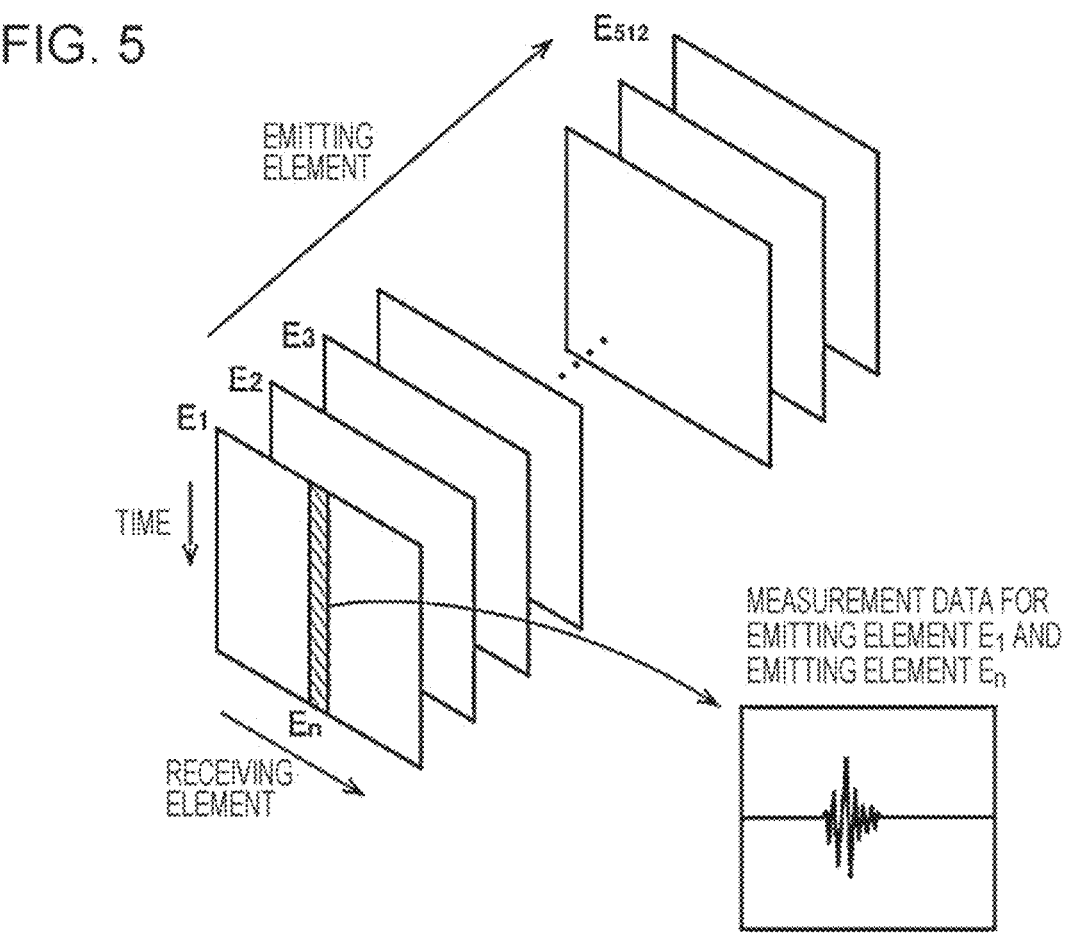
FIG. 5 is a diagram illustrating an example of measurement data.

First, the element specifying unit 131 specifies one emitting element and a plurality of receiving elements positioned opposite to the emitting element. Desirably, the receiving elements are eight or more ultrasonic transducers in total including an ultrasonic transducer that is at a position opposite to the emitting element at which transmitted pulses can be received with high sensitivity and elements adjacent to the ultrasonic transducer. Ultrasonic pulses are emitted from the emitting element, transmitted waves that are propagated through water are received by the receiving elements, and measurement data (waveform signals between the emitting element and the receiving elements) is saved in the memory M. For example, in a case of a ring-shaped ultrasonic probe including 512 elements, in response to emission by one element, transmitted waves are received by 64 elements to obtain waveform signals. When the emitting element is switched to the other elements sequentially to perform emission and reception 512 times, pieces of measurement data for all emitting elements can be obtained (steps S1 and S2). For example, measurement data as illustrated in FIG. 5 is obtained. A receiving element En is any one of the 64 elements that receive transmitted waves.

Next, the transfer characteristic value calculation unit 133 calculates transfer characteristic values and analyzes and diagnoses the emission characteristics and reception characteristics of the elements E (step S3). Examples of each transfer characteristic value include the strength (for example, a peak-to-peak value based on the amplitude), power (for example, the integral of the square), power spectrum (for example, frequency characteristic), and phase of the received signal. For example, for the peak-to-peak value, the maximum value and the minimum value of the amplitude are used, and the peak-to-peak value is calculated by obtaining the difference between the maximum value and the minimum value of the real part of a complex signal obtained by the received signal being subjected to band-pass filtering.

For example, in a diagnosis of the emission characteristic of a certain element E, transfer characteristic values based on 64 received signals corresponding to an emitted signal from the element E are added up and analyzed. In a case where the value obtained as a result of addition is less than or equal to a reference level, any of the element E, an emitter circuit connected to the element E, or the switch circuit can be diagnosed as malfunctioning. Further, a temporary malfunction can also be detected with a method described below. This diagnosis is made for all elements to thereby diagnose all elements, emitter circuits, or the switch circuit. When the transfer characteristic values based on 64 received signals are added up, the emission characteristic of the element E that is an emitting element can be diagnosed even in a case where some of the receiving elements malfunction.

In a diagnosis of the reception characteristic of an element E, transfer characteristic values based on signals received by the element E, that is, based on received signals of pulses emitted from 64 ultrasonic transducers in a direction opposite to the element E, are added up and analyzed. In a case where the value obtained as a result of addition is less than or equal to a reference level, any of the element E, a receiver circuit connected to the element E, or the switch circuit can be diagnosed as malfunctioning. This diagnosis is made for all elements to thereby diagnose all elements, receiver circuits, or the switch circuit. When the transfer characteristic values based on 64 emitted signals are added up, the reception characteristic of the element E that is a receiving element can be diagnosed even in a case where some of the emitting elements malfunction.

For example, the malfunctioning element detection unit 134 detects a malfunctioning element on the basis of peak-to-peak values that serve as the transfer characteristic values (step S4). The malfunctioning element detection unit 134 adds up the peak-to-peak values between each emitting element and all receiving elements. For example, the malfunctioning element detection unit 134 adds up the peak-to-peak values of received signals received by elements E224 to E288 in response to ultrasonic waves emitted by an element E1. The malfunctioning element detection unit 134 determines that an element for which the result of addition is within a predetermined range is normally performing emission, and determines that an element for which the result of addition is outside the predetermined range has its emission function malfunctioning.

The malfunctioning element detection unit 134 adds up a plurality of peak-to-peak values for each receiving element. For example, the malfunctioning element detection unit 134 calculates for the element E1, the peak-to-peak values of received signals in response to ultrasonic waves emitted by elements E257 to E320. The malfunctioning element detection unit 134 determines that an element for which the result of addition is within a predetermined range is normally performing reception, and determines that an element for which the result of addition is outside the predetermined range has its reception function malfunctioning.

The malfunctioning element detection unit 134 determines whether each element is normally functioning or malfunctioning. Further, the malfunctioning element detection unit 134 can classify a malfunctioning element in terms of its malfunctioning function as "malfunctioning only in reception", "malfunctioning only in emission", or "malfunctioning in both emission and reception".

Basically, damage to or degradation of an element E similarly affects both the emission characteristic and the reception characteristic. Therefore, the malfunction state determination unit 135 determines that an element E classified as "malfunctioning in both emission and reception" is damaged or degraded. The malfunction state determination unit 135 determines that the receiver circuit or the switch circuit is malfunctioning in a case of "malfunctioning only in reception" or determines that the emitter circuit or the switch circuit is malfunctioning in a case of "malfunctioning only in emission".

Determination of decreased sensitivity associated with degradation of an ultrasonic transducer will be described. Degradation of an ultrasonic transducer similarly affects emission sensitivity and reception sensitivity. Detection of a decrease in the sensitivity of, for example, the emitting element E1 associated with emission will be described below. The peak-to-peak values of received signal of the elements E257 to E320 in response to ultrasonic waves emitted by the element E1 are added up. The value obtained as a result of addition is compared with measurement data upon shipment, and the element is determined to be degraded in a case where the value is lower than or equal to, for example, a reference value. In a case where malfunctioning elements are found among the 64 receiving elements E257 to E320 in malfunction determination, the value obtained as a result of addition is weighted in accordance with the number and positions of the malfunctioning elements to make an evaluation.

A warning of decreased image quality determined by the ultrasonic imaging system and associated with an element malfunction in the ring-shaped ultrasonic probe will be described.

In the ultrasonic imaging system including the ring-shaped ultrasonic probe, ultrasonic pulses are emitted to a subject present in the ring-shaped ultrasonic probe from a plurality of elements of the ring-shaped ultrasonic probe that are present in a certain direction, and reflected pulses and transmitted pulses from the subject are received by all elements or by a very large number of elements. This emission and reception process is repeatedly performed in all directions of the ring sequentially, and all received signals are used to generate an image. Further, all the received signals are subjected to arithmetic processing in the computer to build an ultrasonic image. Therefore, although image quality attained by the ultrasonic imaging system including the ring-shaped ultrasonic probe is affected by all elements in the ring-shaped ultrasonic probe, abnormalities in some of the elements have a limited impact on image quality.

In the present embodiment, malfunctions in the ring-shaped ultrasonic probe are classified into three patterns described below, and an evaluation criterion for evaluating an impact on image quality in each pattern is established.

Figure 8A:
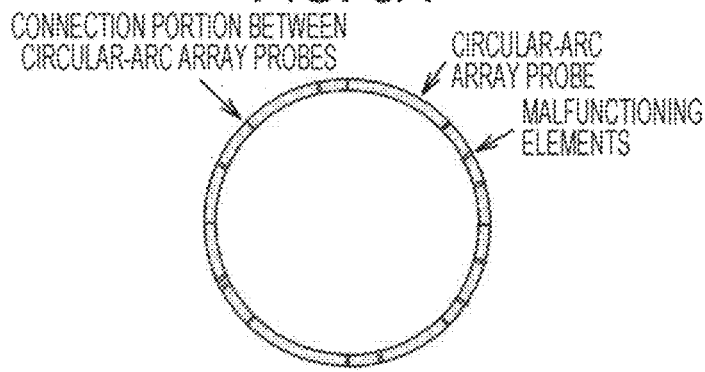
FIG. 8A is a diagram illustrating positional relationships between malfunctioning elements in a ring array transducer.

Pattern 1 is a case where malfunctions occur dispersedly in the ring-shaped ultrasonic probe, an example of which is illustrated in FIG. 8A.

Figure 8B:
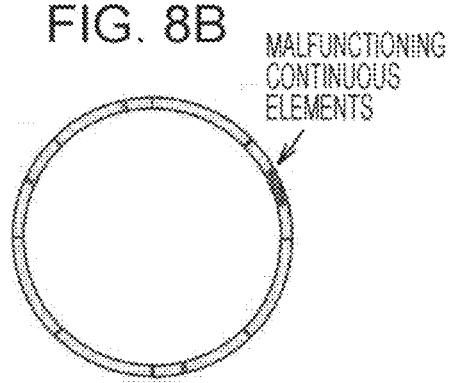
FIG. 8B is a diagram illustrating positional relationships between malfunctioning elements in a ring array transducer.

Pattern 2 is a case where malfunctions occur continuously in the ring-shaped ultrasonic probe, an example of which is illustrated in FIG. 8B.

Figure 8C:
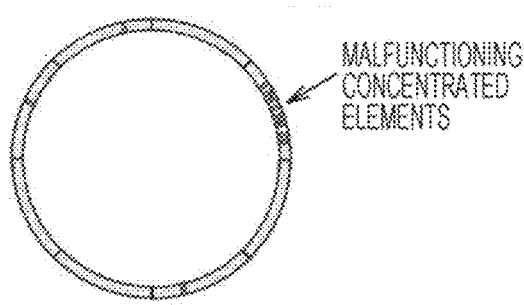
FIG. 8C is a diagram illustrating positional relationships between malfunctioning elements in a ring array transducer.

Pattern 3 is a case where malfunctions occur in a concentrated manner in a local portion in the ring-shaped ultrasonic probe, an example of which is illustrated in FIG. 8C.

The malfunction state determination unit 135 calculates three types of indicators that indicate the malfunction state, namely, the ratio of malfunctioning elements in the entire ring array R, the number of malfunctioning continuous elements, and the ratio of malfunctioning local elements, and determines the malfunction state on the basis of the calculated values (step S5). The malfunction state includes "normal" in which the apparatus can be used without any problems and a high-resolution image can be generated, "warning" in which image quality may decrease to some extent, and "error" in which an image of low image quality is highly likely to be generated.

The malfunction state determination unit 135 compares the ratio of malfunctioning elements in the entire ring array R with predetermined thresholds Th1 and Th2 (Th1<Th2), and determines that the malfunction state is "normal" when the ratio of malfunctioning elements is less than Th1, determines that the malfunction state is "warning" when the ratio of malfunctioning elements is greater than or equal to Th1 and less than Th2, or determines that the malfunction state is "error" when the ratio of malfunctioning elements is greater than or equal to Th2.

Figure 6A:
FIG. 6A is a diagram illustrating the positions of malfunctioning elements.
Figure 6B:
FIG. 6B is a diagram illustrating the positions of malfunctioning elements.

The malfunction state determination unit 135 calculates the number of malfunctioning continuous elements. The number of malfunctioning continuous elements is the number of malfunctioning elements that are continuous (disposed adjacent to each other). For example, in the example illustrated in FIG. 6A, the number of malfunctioning continuous elements is four. In the example illustrated in FIG. 6B, continuity of malfunctioning elements is broken at the element E6, and therefore, the number of malfunctioning continuous elements is three.

Figure 6C:
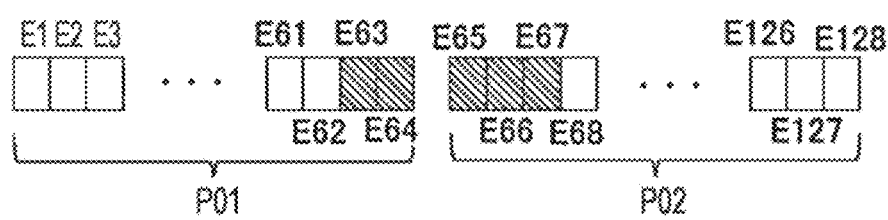
FIG. 6C is a diagram illustrating the positions of malfunctioning elements.

In a case where a plurality of circular-arc array probes are combined, a gap between circular-arc array probes is regarded as, for example, four malfunctioning elements, although this number is determined in accordance with the length of the gap. For example, in the example illustrated in FIG. 6C, four malfunctioning elements are regarded as being present between the element E64 and the element E65, and the number of malfunctioning continuous elements is equal to nine (=2+4+3).

The malfunction state determination unit 135 compares the maximum value of the number of malfunctioning continuous elements in the ring array R with predetermined thresholds Th11 and Th12 (Th11<Th12), and determines that the malfunction state is "normal" when the maximum value of the number of malfunctioning continuous elements is less than Th11, determines that the malfunction state is "warning" when the maximum value of the number of malfunctioning continuous elements is greater than or equal to Th11 and less than Th12, or determines that the malfunction state is "error" when the maximum value of the number of malfunctioning continuous elements is greater than or equal to Th12.

Figure 7A:
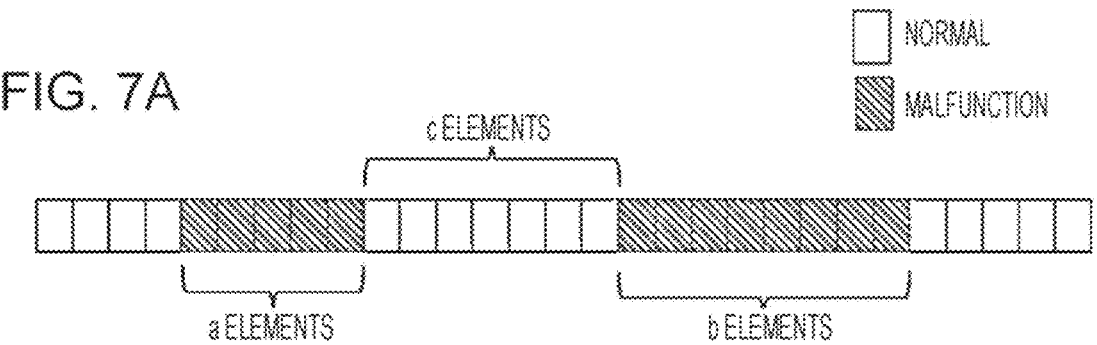
FIG. 7A is a diagram illustrating the positions of malfunctioning elements.

The malfunction state determination unit 135 calculates the ratio of malfunctioning local elements. The ratio of malfunctioning local elements is, in a case where normal elements are sandwiched between malfunctioning elements, the ratio of the malfunctioning elements to the sum of the number of the normal elements sandwiched between the malfunctioning elements (between groups of malfunctioning elements, each of the groups including malfunctioning continuous elements) and the number of the malfunctioning elements (the groups of malfunctioning elements) between which the normal elements are sandwiched. For example, as illustrated in FIG. 7A, in a case where a group of c normal elements is present between a group of a malfunctioning elements and a group of b malfunctioning elements, the ratio of malfunctioning local elements is equal to (a+b)/(a+b+c).

Figure 7B:
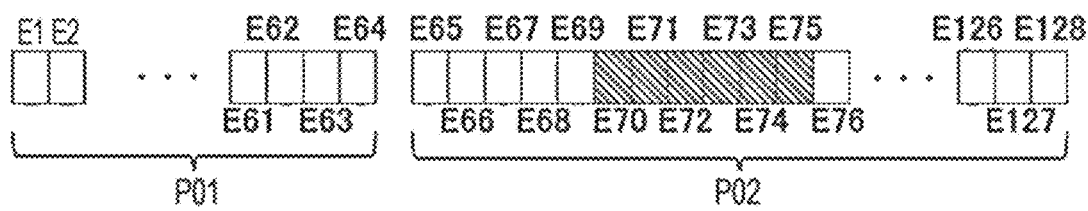
FIG. 7B is a diagram illustrating the positions of malfunctioning elements.

A gap between circular-arc array probes is regarded as four malfunctioning elements. For example, in the example illustrated in FIG. 7B, four malfunctioning elements are regarded as being present between the element E64 and the element E65, and the ratio of malfunctioning local elements is equal to 0.67 (=(4+6)/(4+6+5).

The malfunction state determination unit 135 compares the maximum value of the ratio of malfunctioning local elements in the ring array R with predetermined thresholds Th21 and Th22 (Th21<Th22), and determines that the malfunction state is "normal" when the maximum value of the ratio of malfunctioning local elements is less than or equal to Th21, determines that the malfunction state is "warning" when the maximum value of the ratio of malfunctioning local elements is greater than or equal to Th21 and less than Th22, or determines that the malfunction state is "error" when the maximum value of the ratio of malfunctioning local elements is greater than or equal to Th22.

The malfunction state determination unit 135 may output the result of determination, namely, "normal", "warning", or "error", for each of the three types of indicators that indicate the malfunction state, namely, the ratio of malfunctioning elements in the entire ring array R, the number of malfunctioning continuous elements, and the ratio of malfunctioning local elements, or may output the worst result of determination among the three types of indicators. For example, in a case where the ratio of malfunctioning elements in the entire ring array R is determined to be "normal", the number of malfunctioning continuous elements is determined to be "warning", and the ratio of malfunctioning local elements is determined to be "error", the malfunction state determination unit 135 outputs "error" as the conclusive result of determination.

Figure 9A:
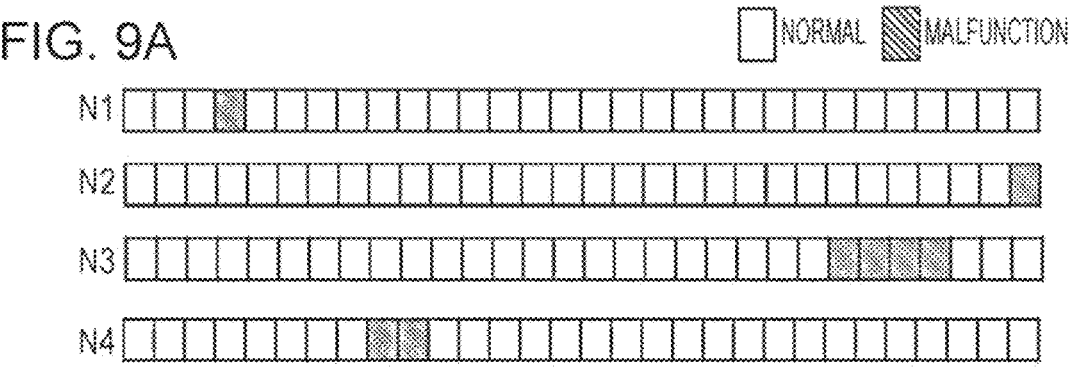
FIG. 9A is a diagram illustrating positional relationships between malfunctioning elements in a case where element malfunctions are detected at random.
Figure 9B:
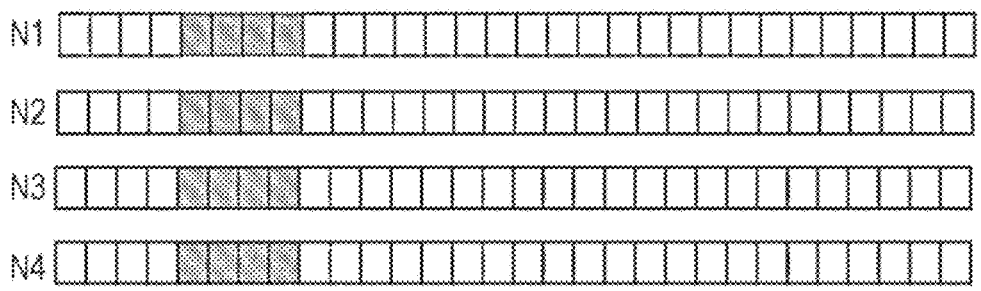
FIG. 9B is a diagram illustrating positional relationships between malfunctioning elements in a case where element malfunctions are cyclically detected.

Determination of a malfunction in emitter-receiver circuits or in the switch circuit will be described. The switch circuit enables efficient control of a large number of emitting-receiving elements with a smaller number of emitter-receiver circuits. The switch circuit connects N emitting-receiving elements per emitter-receiver circuit, connects a certain element to a circuit while switching the certain element, and transfers emitted and received signals. For example, in a case where 512 emitting-receiving elements are controlled by 128 emitter circuits, the switch circuit connects the emitting-receiving elements with the emitter circuits in the ratio of 4:1. In determination of a decrease in the sensitivity of emitting-receiving elements according to the present disclosure, in a case where a decrease in sensitivity cyclically appears once per N times, a malfunction in the switch circuit or in an emitter-receiver circuit that connects the switch circuit with a signal control unit can be identified. In a case where malfunctions occur at random positions as illustrated in FIG. 9A, the malfunctions can be assumed to be caused by emitting-receiving elements or the switch circuit connected to the elements; however, in a case where malfunctions occur cyclically as illustrated in FIG. 9B, the malfunctions can be assumed to be caused by the switch circuit or an emitter-receiver circuit that connects the switch circuit with the signal control unit.

In determination of malfunctioning elements, a malfunctioning portion may be identified as an element, the switch circuit, or an emitter-receiver circuit, and a notification may be given to the user. Repair costs and a measure against a malfunction differ depending on whether a decrease in the sensitivity of the apparatus is caused by an element, an emitter-receiver circuit, or the switch circuit. Specifically, in a case of a malfunction in an element, replacement or repair of the expensive transducer array costs a lot; however, in a case of a malfunction caused by an emitter-receiver circuit, there is the possibility that the malfunction is fixed by maintenance staff replacing the component on site. Accordingly, when a repair portion is identified, repair can be made in a shorter time and more efficiently.

As described above, in the ring-shaped ultrasonic probe, a plurality of circular-arc array probes are combined to form a ring. In terms of capturing an image, the ring is desirably a perfect circle, and the circular-arc array probes are assembled in conformity to a specified precision standard. In the present embodiment, misalignment of a circular-arc array probe is detected. A method for detecting misalignment by using transmitted waves will be described with reference to an example case where the ring-shaped ultrasonic probe is constituted by eight circular-arc array probes illustrated in FIG. 1.

In a case where the water temperature is constant, the propagation time of an ultrasonic pulse between two ultrasonic transducers is in proportion to the distance between the elements. Measurement for one set of circular-arc array probes will be described with reference to an example combination of the circular-arc array probes P01 and P05 illustrated in FIGS. 1. P01 and P05 have a positional relationship in which P01 and P05 face each other. Ultrasonic pulses are emitted from the first element of the circular-arc array probe P01 (emitting end) and are received by all (64) ultrasonic transducers of the circular-arc array probe P05 (receiving end), and the propagation times (ToF) are obtained. The emitting element of P01 is switched to the other elements sequentially, and the propagation times for propagation to the ultrasonic transducers of P05 are measured for every ultrasonic transducer of P01. From the results of measurement, distance information about the distances between the ultrasonic transducers of the circular-arc array probe P01 and those of the circular-arc array probe P05, P01 and P05 forming one set [P01, P05], is obtained.

As combinations for measuring the propagation times for propagation between the circular-arc array probes, 12 sets for which the propagation times can be measured with high accuracy, namely, [P01, P04], [P01, P05], [P01, P06], [P02, P05], [P02, P06], [P02, P07], [P03, P06], [P03, P07], [P03, P08], [P04, P07], [P04, P08], and [P05, P08], are used. For the combination of [P01, P02] for which measurement of the propagation times is difficult because of directivity of pulses, an analysis can be made by using P05 and on the basis of information about [P01, P05] and [P02, P05]. Therefore, from measurement data for the 12 sets, positional information can be obtained for all combinations of the circular-arc array probes.

The propagation time calculation unit 136 calculates propagation times (step S6). For example, the propagation time calculation unit 136 calculates for, for example, the combination of [P01, P04], the propagation times of ultrasonic waves between the elements E1 to E64 included in the circular-arc array probe P01 and elements E193 to E256 included in the circular-arc array probe P04. In this case, the propagation time calculation unit 136 calculates:
the propagation times of ultrasonic waves emitted from the element E1 and received by the elements E193 to E256;
the propagation times of ultrasonic waves emitted from the element E2 and received by the elements E193 to E256;
. . .
the propagation times of ultrasonic waves emitted from the element E64 and received by the elements E193 to E256;
the propagation times of ultrasonic waves emitted from the element E193 and received by the elements E1 to E64;
the propagation times of ultrasonic waves emitted from the element E194 and received by the elements E1 to E64;
. . .
the propagation times of ultrasonic waves emitted from the element E256 and received by the elements E1 to E64.

Note that a malfunctioning element detected by the malfunctioning element detection unit 134 is excluded from the targets of propagation time measurement.

The misalignment detection unit 137 calculates, for each of the combinations of the circular-arc array probes, the average of the differences between the calculated values of propagation times and a reference value, determines the degree of misalignment on the basis of the average for each combination, and detects a circular-arc array probe that is misaligned (step S7).

For example, the misalignment detection unit 137 compares the average for each of the combinations with predetermined thresholds Th31 and Th32 (Th31<Th32), and determines a combination having its average greater than or equal to Th31, if any, to be in the "warning" state in terms of the degree of misalignment, or determines a combination having its average greater than or equal to Th32, if any, to be in the "error" state in terms of the degree of misalignment.

The misalignment detection unit 137 detects, from combinations having its average greater than or equal to the threshold Th31 (or Th32), a circular-arc array probe that is misaligned. For example, in a case where the combinations of [P02, P05], [P02, P06], and [P02, P07] each have its average greater than or equal to the threshold Th31 (or Th32), the misalignment detection unit 137 detects the concave transducer P02 as being misaligned.

Determination of an increase in a noise signal associated with degradation of an ultrasonic transducer will be described. As a cause of an increase in noise in an ultrasonic transducer, for example, the occurrence of unwanted vibration caused by a crack appearing in the element can be considered. Further, the occurrence of crosstalk or an unintended shift in an emission timing can cause noise that is likely to affect an image. Therefore, an increase in noise appears more markedly upon emission in which the ultrasonic transducer strongly vibrates. Detection of an increase in noise upon emission will be described with reference to, for example, the emitting element E1. The frequency analysis unit 138 analyzes the frequencies of received signals received by the elements E257 to E320 in response to ultrasonic waves emitted by the element E1 (step S8). The frequency analysis unit 138 performs Fourier transform on measurement data and calculates a power spectrum. The frequency analysis unit 138 divides the calculated power spectrum into three regions, namely, the band of the elements E, a region higher than or equal to the band, and a region lower than or equal to the band, and saves the regions in the memory M as frequency components.

Each time a self-diagnosis process is performed, a comparison with the frequency components saved in the memory M is made to allow checking of, for example, the occurrence of noise associated with long-term deterioration of the element E1. With the same method, the occurrence of noise and an increase in noise are determined also for the elements E2 to E512.

The determination result output unit 139 outputs the results of determination including the result of determination by the malfunction state determination unit 135 and the result of detection by the misalignment detection unit 137 to the display device 140 to display the results (step S9). For the user to easily determine whether a diagnosis can be made (imaging of the subject can be performed) or whether the apparatus needs to be tuned, the display device 140 may output a warning when the apparatus needs to be tuned. The determination result output unit 139 may calculate the time when maintenance is to be carried out, on the basis of the number of malfunctioning channels or the frequency of occurrence and tell the user or service staff of the manufacturer that "a diagnosis can be made but the recommended time for component replacement comes soon". When a maintenance recommendation notification is thus output in addition to a malfunction notification, the user can schedule a maintenance service systematically and reduce the risks of, for example, a decrease in image quality caused by an unexpected apparatus malfunction and of re-imaging.

As described above, according to the present embodiment, element malfunctions can be automatically detected from measurement data collected by making a plurality of elements receive transmitted waves while switching the emitting element. Further, misalignment of a circular-arc array probe can be detected.

Further, the malfunction state determination unit 135 can determine a malfunction state by using measurement data collected by disposing a scatterer in the imaging region. In relation to the accuracy of emitter-receiver circuits and the switch circuit, the number of instantaneous failures increases gradually due to long-term deterioration, instantaneous failures frequently occur at the end, and an impact on image quality is not negligible. An instantaneous failure is a failure that is not observed in a regular inspection made once a day but is a failure that unexpectedly occurs on any of the occasions of imaging performed on the day, followed by spontaneous restoration to a normal state. This type of failure does not necessarily leads to an irreversible change at the end but is to be regarded as a malfunction when the failure occurs frequently even if the failure sometimes occur and sometimes does not occur.

An instantaneous failure as described above is less likely to lead to a critical decrease in the image quality of a rebuilt ultrasonic CT image as long as the frequency of occurrence is low. However, an increase in the frequency of occurrence of such an instantaneous failure is suggestive of circuit degradation. Therefore, when the result of determination on each occasion of imaging is combined with the result of malfunction determination performed once a day, the user of the apparatus can predict a malfunction more accurately.

Figure 10:
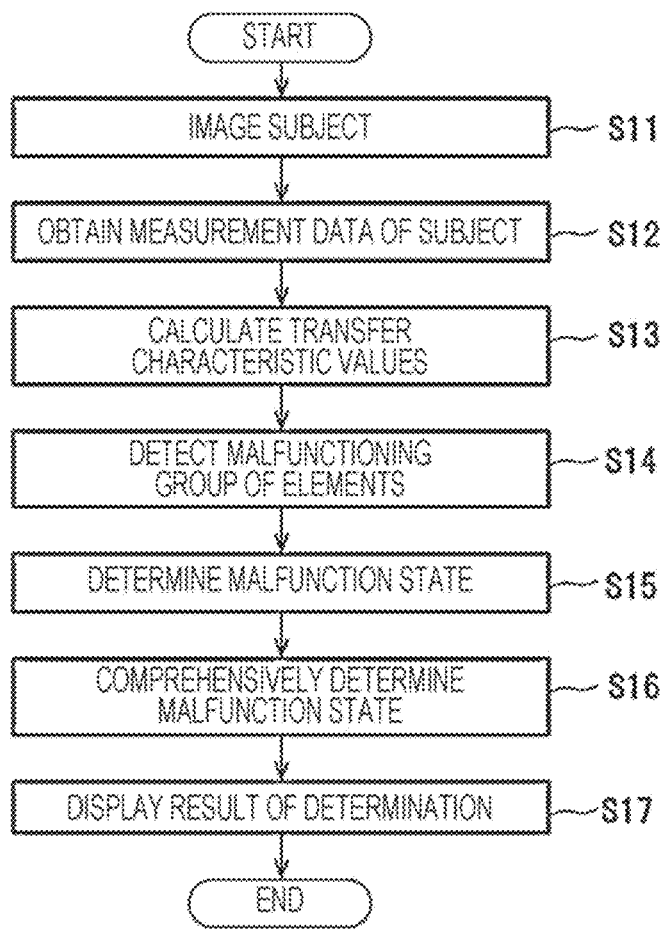
FIG. 10 is a flowchart for explaining a self-diagnosis method by the ultrasonic imaging system.

An example where measurement data obtained by imaging a subject is used and malfunction determination is performed on each occasion of imaging will be described with reference to the flowchart illustrated in FIG. 10. Measurement data obtained by imaging a subject includes transmitted waves that are transmitted through the subject and scattered waves that are scattered by the subject. In the present embodiment, measurement data obtained not only from transmitted waves but also from scattered waves including reflected waves can be used in malfunction determination. It is assumed that the ring array R that is a combination of the circular-arc array probes P01 to P08 illustrated in FIG. 1 is used in imaging of a subject.

In an imaging process for a subject (step S11), first, the arithmetic device 130 selects the circular-arc array probe P01 as a group of emitting elements. The circular-arc array probe P01 is hereinafter also referred to as the group of emitting elements P01. The emitter-receiver circuit 120 makes the group of emitting elements P01 emit ultrasonic waves having a predetermined waveform. The arithmetic device 130 similarly selects a group of receiving elements, and the switch circuit 110 switches a position in the group of receiving elements. For example, in a case where the ring array is constituted by 512 elements E and where 128 elements are selected as receiving elements for a single emission operation, when reception in all directions is performed while the position of the group of receiving elements is shifted by the switch circuit 110 by eight elements, emission is performed 64 times from the group of emitting elements P01. The group of receiving elements receives transmitted waves and scattered waves generated on each occasion of emission.

When emission and reception are repeated similarly while the group of emitting elements is switched from the circular-arc array probe P01 up to the circular-arc array probe P08, measurement data of one cross-sectional slice is obtained (step S12). This measurement data is converted to two-dimensional data constituted by received signals obtained by each of the groups of emitting elements P01 to P08. After completion of obtaining measurement data for one slice, the position of the ring array is moved upward or downward by the stepping motor to move the imaging slice plane. When pieces of measurement data of a plurality of slices are thus obtained sequentially, volume data of the entire subject is obtained.

In a case where any of the elements E is malfunctioning, the measurement data includes a blank region in which no signal is received due to lack of the element. Such a malfunction is often everlasting, and therefore, once the malfunction is observed, the malfunction is similarly observed in all subsequent slices. A malfunctioning element is detected in a regular inspection made once a day. In contrast, in a case where the switch circuit or an emitter-receiver circuit has a failure, for measurement data of one slice, only a specific group of emitting elements or group of receiving elements receive signals different from the other measurement signals. However, in a case of an instantaneous failure caused by an electric signal in a circuit, such a failure might not occur upon imaging of subsequent slices. Therefore, detection of a malfunction state from each piece of obtained measurement data is effective.

In malfunction determination using measurement data obtained upon imaging of a subject, for example, for measurement data of each slice, the difference in measurement data between groups of emitting elements is calculated. In a case where the switch circuit or an emitter-receiver circuit has a failure, continuity of only measurement data for a specific group of emitting elements (for example, P05) is broken at the boundary with measurement data for the adjacent groups of emitting elements (P04 and P06). Examples of the continuity include continuity between emitted waveforms, continuity between slices, and continuity between emitting or receiving transducer blocks. The transfer characteristic value calculation unit 133 calculates breaks in these types of continuity (step S13), the malfunctioning element detection unit 134 identifies a malfunctioning group of elements (block) and a malfunctioning element (step S14), and the malfunction state determination unit 135 determines the malfunction state (step S15).

When the emission condition is changed upon imaging of a subject, measurement data for a different purpose is obtained. For example, of ultrasonic imaging, harmonic imaging, Doppler blood flow imaging, elastography, and so on allow measurement of a blood flow or elasticity in addition to the structure of a subject and a diagnosis of the nature or physical property of tissue by repeating emission and reception a plurality of times in measurement of the same region. In a case where measurement of one region is thus performed by performing emission and reception a plurality of times, more detailed malfunction determination can be performed by using a plurality of pieces of obtained measurement data.

Figure 11:
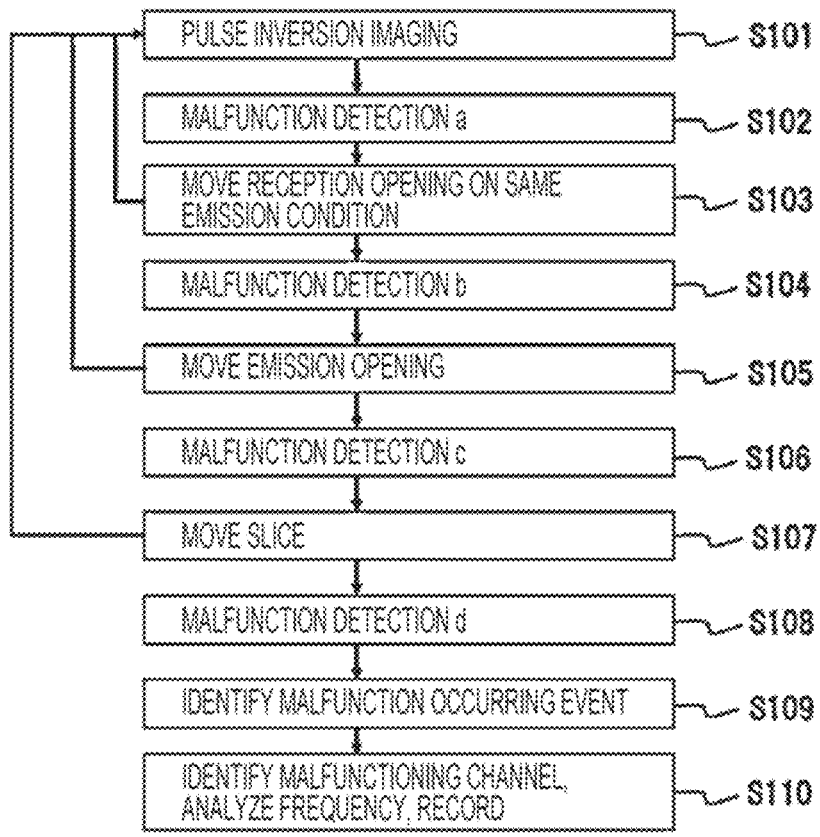
FIG. 11 is a flowchart for explaining a self-diagnosis method by the ultrasonic imaging system.

FIG. 11 illustrates an example where malfunction detection in a plurality of imaging modes (malfunction detection a to malfunction detection d) is performed in the order of imaging. Of ultrasonic imaging, in a publicly known pulse inversion process, Doppler blood flow imaging, or elastography, imaging is performed a plurality of times on the same emission condition, with the same reception opening, and with the same or different waveforms (step S101). In such a case, an event (unexpected and unintended emission or crosstalk having low reproducibility) that is less likely to be repeatedly reproduced is detected in a malfunction detection process a (step S102). For example, in the pulse inversion process, for an output obtained by combining a positive waveform and a negative waveform, the frequency band of the signal is monitored to thereby enable detection of emission having been performed without malfunction-causing positive-negative inversion. In a case where, for example, Doppler imaging in which the same waveform is repeated, a significant change only in a specific time domain (specific depth), if any, can be regarded as a malfunction.

In a case where the number of channels N2 of the electric circuit is smaller than the number of receiving elements N1, reception needs to be repeated (N2/N1) times on the same emission condition while the reception opening is moved (step S103). Emission that is not reproduced at this time can be detected in a malfunction detection process b as a malfunction (step S104). Similarly, a malfunction can be detected in a malfunction detection process c in which a comparison is made between before and after changing the emission condition (steps S105 and S106) and in a malfunction detection process d in which a comparison is made between before and after movement of the slice position (steps S107 and S108).

When imaging of the entire volume of the subject is completed, an event (related to the slice position, the emission condition, or the reception opening) in which a malfunction occurs is identified (step S109), and further, a channel of the electric circuit in which a malfunction occurs can be identified (step S110).

Figure 12A:
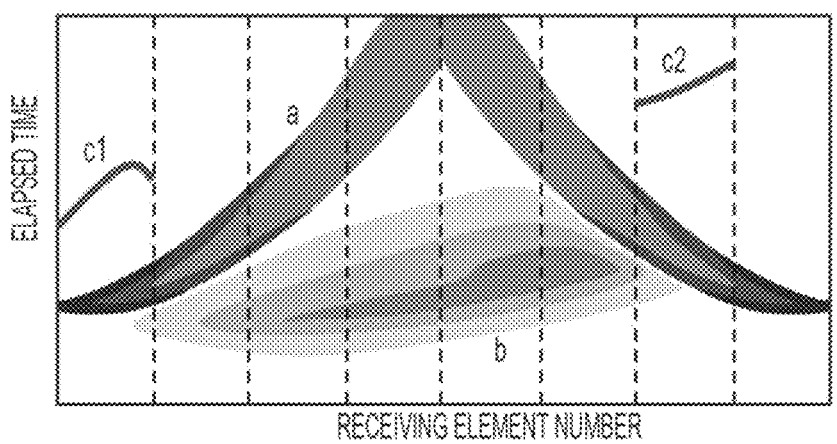
FIG. 12A is a matrix chart of the signal strength in an imaging region.
Figure 12B:
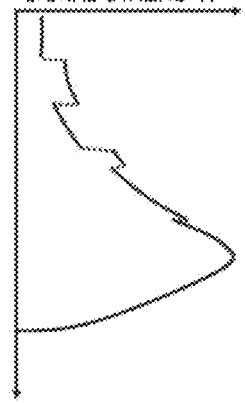
FIG. 12B is a view of projection along the vertical axis and the horizontal axis.
Figure 12C:
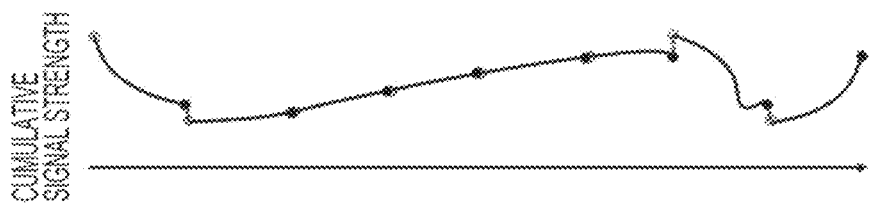
FIG. 12C is a view of projection along the vertical axis and the horizontal axis.

FIG. 12A is a matrix chart showing continuity of measurement data of a certain slice, and FIGS. 12B and 12C are views of projection along the vertical axis and the horizontal axis. The horizontal axis represents the receiving element number (from 1 to N1), and the vertical axis represents the elapsed time from emission to reception of signals (from 1 to M). The gray scale represents the strengths of signals subjected to envelope detection, a and b represent transmitted waves and scattered waves respectively, and c1 and c2 correspond to records of unintended emission waveforms caused by malfunctions.

FIG. 12A illustrates a case where (N2/N1) is equal to eight, and each vertical dotted line represents the boundary of signals received in a single emission operation. In a case where the apparatus is normally functioning, both transmitted waves and scattered waves are continuously distributed across the dotted lines. In contrast, in a case where emission is performed unexpectedly, repeated reproducibility does not appear between the i-th emission and the i+1-th emission, and therefore, the signals are discontinued in the portion of the dotted line. The discontinuous signals can be detected in, for example, the malfunction detection processes b, c, and d (see FIG. 11) by using the difference or a statistical process (deviation from the average or a large distribution). Each of the signal waveforms c1 and c2 is a function determined by the geometrical positional relationship between the emitting element and the receiving element, and therefore, the emitting element number of an emitting element in which unintended emission occurs (and a corresponding channel of the electric circuit) can be identified by, for example, a fitting process.

Retaining all reception data uses up a memory mounted in the product and might not be desirable. The two plots in FIG. 12B and FIG. 12C are plots obtained by performing an add-up process in the direction of receiving elements (FIG. 12B) and in the direction of the elapsed time (FIG. 12C) respectively. Conversion to these two waveforms subjected to the cumulative process can reduce the data volume from N1×M to N1+M. In a case where, for example, N1 and M are numbers of the similar order, data can be reduced to $2M/M^2=2/M$ of the original volume.

On these cumulative waveforms, discontinuous portions can be extracted. In a case where the cumulative process is performed, an emission event in which unintended emission occurs can be identified, but the element number and a corresponding channel number of the electric circuit are unable to be detected. This function is for only easily monitoring the frequency of occurrence of unintended emission. With reference to FIG. 12C, discontinuous portions are identified in advance, and therefore, regarding the waveform obtained by the cumulative process in the direction of the elapsed time, data for all receiving element numbers need not be retained, and retaining only waveform data for receiving elements adjacent to each other with a dotted line therebetween is also effective. Each white dot and a corresponding black dot in FIG. 12C represent the respective ends of a signal. Determination of continuity can be performed between the right end (receiving element number N1) and the left end (receiving element number 1).

A malfunction state is determined in accordance with, for example, a threshold of the difference in measurement data between groups of emitting elements and the frequency of occurrence. For example, the difference between groups of emitting elements is defined as 1 in a case where reception of a signal not continuous with signals in both the adjacent groups of emitting elements is observed, and is defined as 0 in a case where such an event is not observed. As the frequency of occurrence, the number of malfunction states, occurring for all slices, obtained on each occasion of imaging is stored, and the tendency of increases or decreases in the rate of malfunction state occurring per day is calculated.

A malfunction state determined on each occasion of imaging is stored in a memory. For example, at the end of an operation on the day, the malfunction state determination unit 135 may perform comprehensive determination of a malfunction state by using the result of determination of a malfunction state performed in the morning of the day on which the result of determination is obtained and by using the result of determination of a malfunction state performed on each occasion of imaging (step S16), and the determination result output unit 139 may display the result of comprehensive determination (step S17). When the frequency of a malfunction state upon imaging is high, the result of determination indicating that degradation becomes serious and the need for a circuit inspection service is increasing is displayed.

When self-determination of a malfunction state of transducers is performed regularly as described above, maintainability of the apparatus increases and automatic imaging can be performed safely.

When the apparatus verifies measurement data on each occasion of imaging during a medical examination and determines an apparatus malfunction state, validity of the obtained data can be automatically calculated. For example, in a case of using the apparatus outside a hospital, such as in a medical examination facility or a medical examination bus, a laboratory technician or a diagnostician is unable to check captured images on site. Such a case involves a risk of imaging being continued without awareness of a malfunction in the apparatus. Specifically, in a case of, for example, a medical examination bus in which the apparatus undergoes vibration during traveling, the frequency of occurrence of a failure in the transducer array increases. In the present embodiment, the apparatus itself performs automatic malfunction determination, determines whether to continue imaging, stops imaging in a case where imaging is difficult, and performs a step of calculating and displaying the maintenance time, which can reduce a risk of, for example, redoing a medical examination.

As a measure against a malfunction, the apparatus basically needs to be designed so that a malfunction does not occur in a use environment in which the apparatus undergoes, for example, vibration. In addition to the design, data quality is monitored to thereby allow doubled safety.

In the above-described embodiment, when noise determination based on a frequency analysis and the result of detecting misalignment in the array are used, a comprehensive malfunction diagnosis can be made.

In the above-described embodiment, in a case where a malfunctioning element is detected, an ultrasonic CT image may be rebuilt without using the malfunctioning element in emission or reception of ultrasonic waves. Alternatively, an ultrasonic CT image may be rebuilt by estimating and interposing measurement data of the malfunctioning element from measurement data of normal elements around the malfunctioning element.

In the above-described embodiment, an acoustic transfer characteristic or a malfunction diagnosis result may be saved to record changes over time. When changes over time are recorded, the course of an increase in the number of malfunctioning elements or an increase in noise is checked, and the time when a malfunction diagnosis is to be made is predicted, maintainability can be increased.

Note that the present disclosure is not limited to the above-described embodiment, and configuration elements can be modified and embodied in the stage of implementation without departing from the gist of the present disclosure. A plurality of configuration elements disclosed in the above-described embodiment can be combined as appropriate. For example, some configuration elements among all configuration elements described in the embodiment may be removed. Further, configuration elements in different embodiments may be combined as appropriate.

What is claimed is:

1. A malfunction inspection method for an ultrasonic imaging system including an array transducer that includes a plurality of elements each performing at least one of emission or reception of ultrasonic waves, at least some of the plurality of elements being disposed so as to face each other, comprising:
specifying one emitting element among emitting elements that emit the ultrasonic waves and a group of receiving elements that are at least some of the plurality of elements and that receive transmitted waves emitted from the one emitting element and transmitted through an imaging region;
collecting measurement data of the transmitted waves via the group of receiving elements while switching the one emitting element, wherein the group of receiving elements receives the transmitted waves directly from the one emitting element;
calculating transfer characteristic values from the measurement data; and
detecting a malfunctioning element among the plurality of elements based on the transfer characteristic values.

2. The malfunction inspection method according to claim 1, further comprising:
calculating at least one of an emission characteristic of each of the emitting elements or a reception characteristic of each of the receiving elements; and
detecting the malfunctioning element based on at least one of the emission characteristic or the reception characteristic.

3. The malfunction inspection method according to claim 2, further comprising:
calculating the emission characteristic for each of the emitting elements based on a plurality of pieces of the measurement data collected via the group of receiving elements; and
calculating the reception characteristic for each of the receiving elements based on a second plurality of pieces of the measurement data collected in response to the emission by the emitting elements.

4. The malfunction inspection method according to claim 2, further comprising:
controlling, via a switch, the emission and the reception of the ultrasonic waves by the plurality of elements; and
determining a malfunction state of the plurality of elements based on the emission characteristic and the reception characteristic.

5. The malfunction inspection method according to claim 1, wherein the transfer characteristic values each include at least one of a strength, a power, a frequency characteristic, a propagation time, or a phase of a received signal in the measurement data.

6. The malfunction inspection method according to claim 1, wherein a malfunction state is determined based on at least one of a number or positions of malfunctioning elements.

7. The malfunction inspection method according to claim 1, wherein the array transducer includes at least three or more circular-arc ultrasonic array probes each including a group of elements, the method further comprising:
calculating propagation times of the transmitted waves from the measurement data; and
detecting misalignment of the at least three or more circular-arc ultrasonic array probes from the propagation times.

8. The malfunction inspection method according to claim 7, further comprising:
emitting first ultrasonic waves while a first emitting element in a first circular-arc ultrasonic array probe is switched, and collecting second measurement data of second transmitted waves via a second plurality of elements of a second circular-arc ultrasonic array probe different from the first circular-arc ultrasonic array probe; and
switching a combination of one circular-arc ultrasonic array probe that emits the ultrasonic waves and another circular-arc ultrasonic array probe that receives the transmitted waves.

9. A malfunction inspection method for an ultrasonic imaging system including an array transducer that includes a plurality of elements each performing at least one of emission or reception of ultrasonic waves, at least some of the plurality of elements being disposed so as to face each other, comprising:
specifying one emitting element among emitting elements that emit the ultrasonic waves and a group of receiving elements that are at least some of the plurality of elements and that receive transmitted waves emitted from the one emitting element and transmitted through an imaging region;
collecting measurement data of the transmitted waves via the group of receiving elements while switching the one emitting element;
calculating transfer characteristic values from the measurement data; and
detecting a malfunctioning element among the plurality of elements based on the transfer characteristic values,
wherein a malfunction state is determined based on a number of malfunctioning elements that are continuous.

10. The malfunction inspection method according to claim 9, wherein a ratio of malfunctioning local elements is calculated by using a number of normal elements sandwiched between the malfunctioning elements and the number of the malfunctioning elements between which the normal elements are sandwiched, and wherein the malfunction state is determined based on the ratio of malfunctioning local elements.

11. The malfunction inspection method according to claim 9, wherein the ultrasonic imaging system includes emitter-receiver circuits controlling the emission and the reception of the ultrasound waves at the plurality of elements via a switch circuit, the method further comprising:
emitting the ultrasonic waves to a subject disposed in the imaging region while the one emitting element is switched, and collecting subject measurement data including scattered waves by using the group of receiving elements; and
determining the malfunction state of the plurality of elements or the switch circuit based on the measurement data and the subject measurement data.

12. An ultrasonic imaging system, comprising:
an array transducer that includes a plurality of emitter-receivers each performing at least one of emission or reception of ultrasonic waves, at least some of the plurality of emitter-receivers being disposed so as to face each other; and circuitry configured to:
- specify one emitter among emitters that emit the ultrasonic waves and a group of receivers that are at least some of the plurality of emitter-receivers and that receive transmitted waves emitted from the one emitter and transmitted through an imaging region;
- collect measurement data of the transmitted waves via the group of receivers while switching the one emitter, wherein the group of receivers receives the transmitted waves directly from the one emitter;
- calculate transfer characteristic values from the measurement data; and
- detect a malfunctioning emitter-receiver among the plurality of emitter-receivers based on the transfer characteristic values.

* * * * *